United States Patent
Reyes et al.

(10) Patent No.: US 7,997,277 B2
(45) Date of Patent: Aug. 16, 2011

(54) FENESTRATED EXTREMITY SURGICAL DRAPE

(75) Inventors: Rogelio Reyes, El Paso, TX (US); Mylena S. Holguin, Chicago, IL (US); Art Sainz, Santa Teresa, NM (US); Jesus R. Loya, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 26 days.

(21) Appl. No.: 12/542,305

(22) Filed: Aug. 17, 2009

(65) Prior Publication Data

US 2009/0301632 A1 Dec. 10, 2009

Related U.S. Application Data

(62) Division of application No. 11/245,882, filed on Oct. 7, 2005, now Pat. No. 7,594,512.

(51) Int. Cl.
*A61B 19/08* (2006.01)
(52) U.S. Cl. .......................................... 128/853
(58) Field of Classification Search ........... 128/849–853
See application file for complete search history.

(56) References Cited

U.S. PATENT DOCUMENTS

| | | | |
|---|---|---|---|
| 3,956,048 A | 5/1976 | Nordgren | |
| 4,027,665 A | 6/1977 | Scrivens | |
| 4,081,306 A | 3/1978 | DePriest et al. | |
| 4,730,609 A | 3/1988 | McConnell | |
| 4,890,628 A | 1/1990 | Jackson | |
| 4,974,604 A * | 12/1990 | Morris ........................... | 128/853 |
| 5,038,798 A | 8/1991 | Dowdy et al. | |
| 5,161,544 A | 11/1992 | Morris | |
| 5,222,507 A | 6/1993 | Taylor | |
| 5,345,946 A | 9/1994 | Butterworth et al. | |
| 5,388,593 A | 2/1995 | Thomalla | |
| 5,394,891 A | 3/1995 | Mills et al. | |
| 5,398,700 A | 3/1995 | Mills et al. | |
| 5,538,012 A | 7/1996 | Wiedner et al. | |
| 5,592,952 A | 1/1997 | Bohn | |
| 5,682,618 A | 11/1997 | Johnson et al. | |
| 5,778,891 A | 7/1998 | McMahan | |
| 5,832,925 A | 11/1998 | Rothrum | |
| 5,879,493 A | 3/1999 | Johnson et al. | |
| 6,213,124 B1 | 4/2001 | Butterworth | |
| 6,694,981 B2 | 2/2004 | Gingles et al. | |
| 6,705,324 B1 | 3/2004 | Petersvik | |
| 6,725,864 B2 | 4/2004 | Ewonce et al. | |
| D498,536 S | 11/2004 | Ewonce et al. | |
| 2003/0121522 A1 | 7/2003 | Gingles et al. | |
| 2003/0196668 A1 | 10/2003 | Harrison et al. | |

FOREIGN PATENT DOCUMENTS

EP 0 631 760 A2 1/1995

\* cited by examiner

*Primary Examiner* — Patricia M Bianco
*Assistant Examiner* — Tarla R Patel
(74) *Attorney, Agent, or Firm* — Arent Fox LLP

(57) ABSTRACT

A method of forming a fenestrated extremity surgical drape includes providing improved seal integrity to reduce the occurrence of pathogenic contamination at the surgical site via migration through the seal. The seal has a non-linear configuration to eliminate uneven stress concentrations commonly located at the corners of rectilinear seals. An elastomeric apertured panel can be disposed between a film panel and a fiber/film laminate panel. These layers can be joined by a heat sealing operation along two spaced apart concentric seal locations ringing the aperture and a fenestration in the laminate panel. The assembly can then be affixed by adhering the underside(s) of one or more panels to a base drape, which has an opening aligned with the aperture and fenestration.

8 Claims, 4 Drawing Sheets

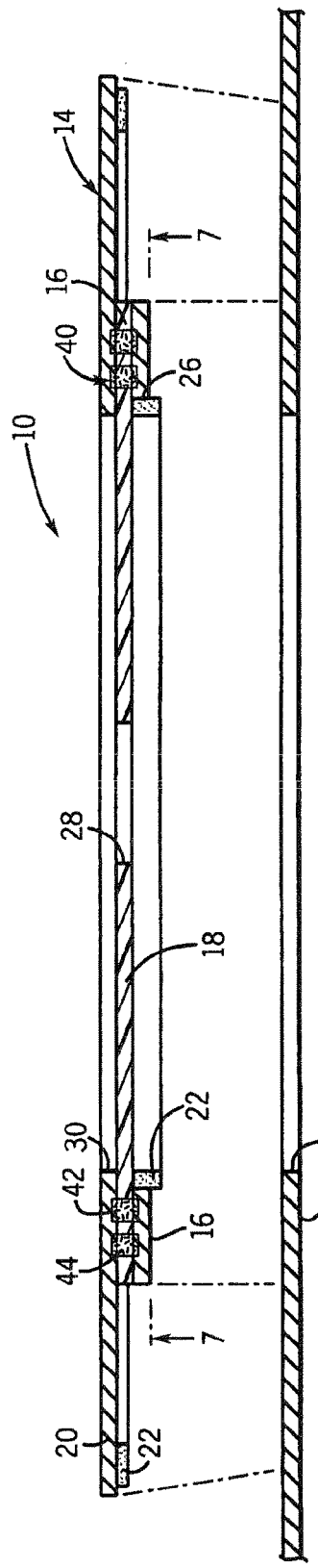
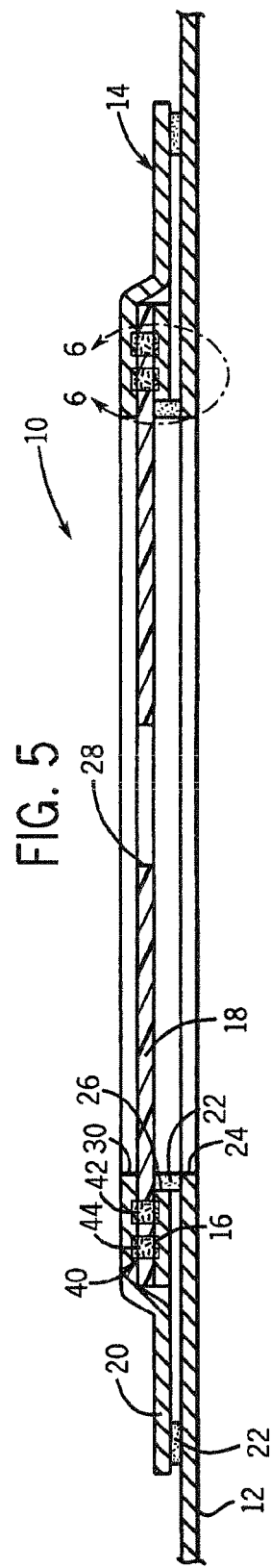

FENESTRATED EXTREMITY SURGICAL DRAPE

CROSS-REFERENCE TO RELATED APPLICATIONS

This application is a divisional application of U.S. application Ser. No. 11/245,882, filed Oct. 7, 2005, the disclosure of the prior application is hereby incorporated in its entirety by reference.

STATEMENT OF FEDERALLY SPONSORED RESEARCH OR DEVELOPMENT

Not applicable.

BACKGROUND OF THE INVENTION

1. Technical Field

The present invention relates to the field of medical items used during surgery. In particular, the invention pertains to an improved fenestrated surgical drape.

2. Description of the Related Art

Surgical drapes are used during surgery to create a sterile barrier around the surgical site. Surgical drapes having fenestrations, or openings, that are specifically designed for certain surgical procedures are well known. Typically, such drapes are structured with pre-shaped and pre-sized openings in contemplation of providing surgical access to a specific anatomical site of the patient. In this category of drape, the fenestration or opening is used for surgical access.

Another type of fenestrated drape is that which is configured to accommodate the anatomy through the fenestration but also to create the sterile field between the body portion containing the surgical site and the remainder of the patient's body via a conformable aperture. Thus, in this type of surgical drape, the fenestration provides surgical access and the aperture provides surgical isolation by sealing against the patient's body. One example of this type of fenestrated drape is one in which the aperture is elastomeric and generally dimensioned to accommodate a limb or other anatomical extension. Thus, when the limb is inserted through the opening, minor variations in natural geometry are accommodated by the flexibility of the elastomeric material. The elastomeric material further forms a tight seal circumscribing the anatomy, thereby forming a sterile barrier separating the surgical site from the remainder of the patient's body. Elastomeric aperture type fenestrated drapes afford the advantage of creating a secure air and fluid barrier between the sterile and non-sterile sites without requiring the use of supplemental tourniquets, taping and the like.

Current such fenestrated drapes are constructed by superimposing panels and portions of materials to seal the apertured panel to the base drape. The seal between the layers is conventionally formed using adhesives, such as double-sided adhesive areas to create a "square" seal around the perimeter of the aperture and the opening in the base drape.

One problem associated with current fenestrated surgical drapes is the risk of compromising the sterile field at the surgical site. In particular, although the elastomeric fit circumscribing the limb or other anatomical extension reduces the likelihood of contamination through the immediate area around the aperture, the perimeter of the apertured panel is still nevertheless dependent upon the adhesive between layers for the microbial barrier. Fluid, for example, can potentially transport across the adhesive seal between the layers surrounding the apertured panel.

Another problem with current fenestrated drapes, particularly with apertured panels incorporated into the drape, involves structural integrity. That is to say, current designs experience stress points during their use at certain locations around the perimeter of the attachment sites. On occasion, the stress results in separation of the seams at these sites, thereby compromising the sterile field surrounding the surgical site. Accordingly, the risk of exposure and infection at the surgical site is increased.

There is thus a need in the field of surgical drapes for a drape having an aperture with improved structural integrity and microbial barrier properties at the seal.

SUMMARY OF THE INVENTION

The invention provides a fenestrated surgical drape for use with body extremities that has improved seal integrity to reduce the occurrence of pathogenic contamination at the surgical site via migration through the seal. The seal can have a non-linear configuration that eliminates uneven stress concentrations commonly located at the corners of rectilinear seals. A heat sealing operation can be used to create two or more spaced apart seal locations to provide redundant, higher integrity sealing with greater uniformity throughout the seal.

Specifically, one aspect of the invention provides a fenestrated surgical drape having a base drape and a multi-panel assembly including a sealing panel with an opening, an apertured panel and a fenestrated panel. The panels are aligned so that the opening, aperture and fenestration are superimposed in registration with one another, and then collectively joined to one another to form a continuous fluid impervious seal surrounding the aperture and fenestration. The panel assembly is fixed to the base drape about the entire perimeter of the base drape opening so that it is superimposed in registration with the sealing panel opening, the aperture and the fenestration.

The apertured panel can be made of an elastomeric material so that it can stretch, conform and seal against an extremity of the body. In this way, the present invention provides a surgical drape suited for use with a body extremity to form a sterile barrier separating the surgical site from the remainder of the patient's body without the need for supplemental isolation devices.

The apertured panel can be disposed between the sealing panel and the fenestrated panel. All three panels, once properly aligned, can be joined together as an assembly. The assembly can then be fixed to the base drape such as by an adhesive between one or more panels and the base drape about the opening of the base drape.

Multiple distinct seal regions can be provided about the sealing panel opening, the aperture and the fenestration, which can be effected by heat sealing operation using heat and pressure to thermally and mechanically bond the panels together. Non-linear seal regions eliminate the hot spots associated with rectilinear seals formed by the application of heat. For example, two concentric circular seal regions can ring the aperture and fenestration, the seal regions being spaced apart some radial distance. A more uniform seal is achieved in this manner by eliminating the hot spots associated with corners, and by employing multiple seal regions, individually of smaller dimension than if a single large seal. With smaller sized individual seals, smaller dimensioned dies can be used, the wall(s) of which can be heated more uniformly so that cold spots therein are avoided. Moreover, multiple seal regions, each individually surrounding the aperture and the fenestration and the outer seal region(s) surrounding the inner seal region(s), provide redundant sealing to better reduce the likelihood of contaminants breaching the seal.

Another aspect of the invention provides a fenestrated surgical drape, suitable for use with human extremities, including a base drape substrate and a multi-layer panel assembly including a film sealing panel, an elastomeric apertured panel and a fiber/film fenestrated panel. The assembly can be affixed to the base drape with an adhesive, and the base drape can itself be an assembly of substrates, such as non-woven fibrous material and film, for example a spunbonded/film/ spunbonded laminate. The surgical drape can thus be arranged in the order of the spunbonded/film/spunbonded base drape, adhesive, film panel, elastomeric panel and fiber/ film panel with its film side facing the elastomeric panel.

Another aspect of the invention provides a method of making a fenestrated surgical drape. The method includes forming a panel assembly having a sealing panel with an opening, a fenestrated panel defining a fenestration, and an apertured panel defining an aperture and disposed between the sealing and fenestrated panels. The panels are superimposed such that the sealing panel opening, the fenestration and the aperture are aligned in registration. The panels are joined by heat sealing along a seal surrounding the aperture and fenestration. The panel assembly is affixed to the base drape so that the sealing opening, the fenestration and the aperture are superimposed in registration with the base drape opening.

The above and still other advantages of the invention will be apparent from the detailed description and drawings. What follows are one or more preferred embodiments of the present invention. To assess the full scope of the invention the claims should be looked to as the preferred embodiment(s) are not intended to be exclusively within the scope of the invention.

BRIEF DESCRIPTION OF THE DRAWINGS

FIG. 4 is a sectional view taken through an aperture along line 4-4 of FIG. 3 showing the surgical drape of the present invention before the panel assembly is affixed to the base drape;

FIG. 5 is a sectional view similar to FIG. 4 albeit with the panel assembly affixed to the base drape;

DETAILED DESCRIPTION OF THE PREFERRED EMBODIMENT(S)

Figure 1:
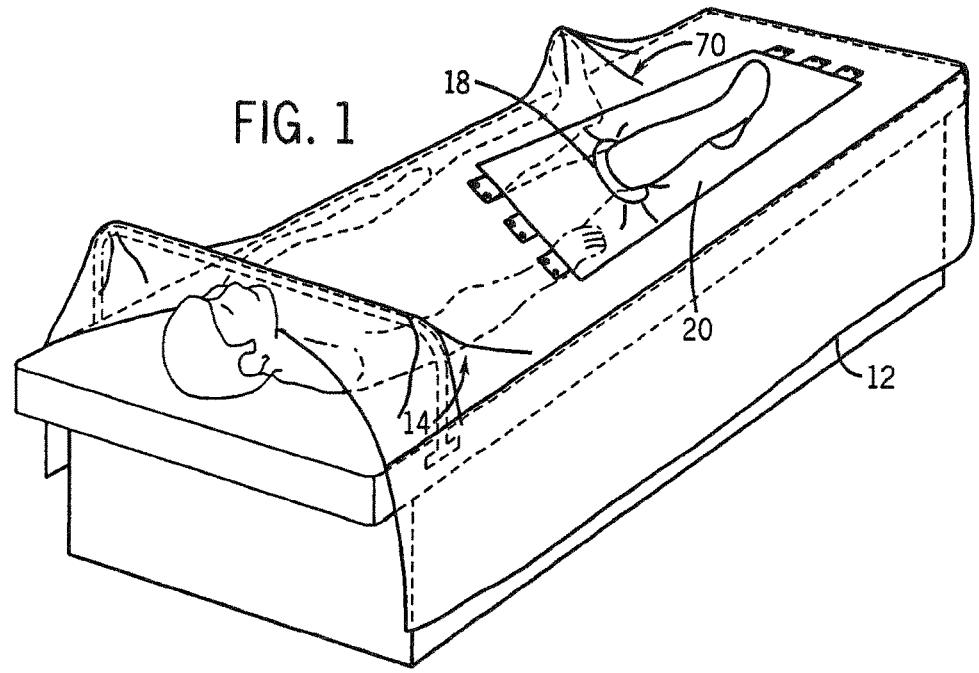
FIG. 1 is a perspective view of a patient on a surgical table draped in a fenestrated extremity surgical drape according to the present invention.
Figure 2:
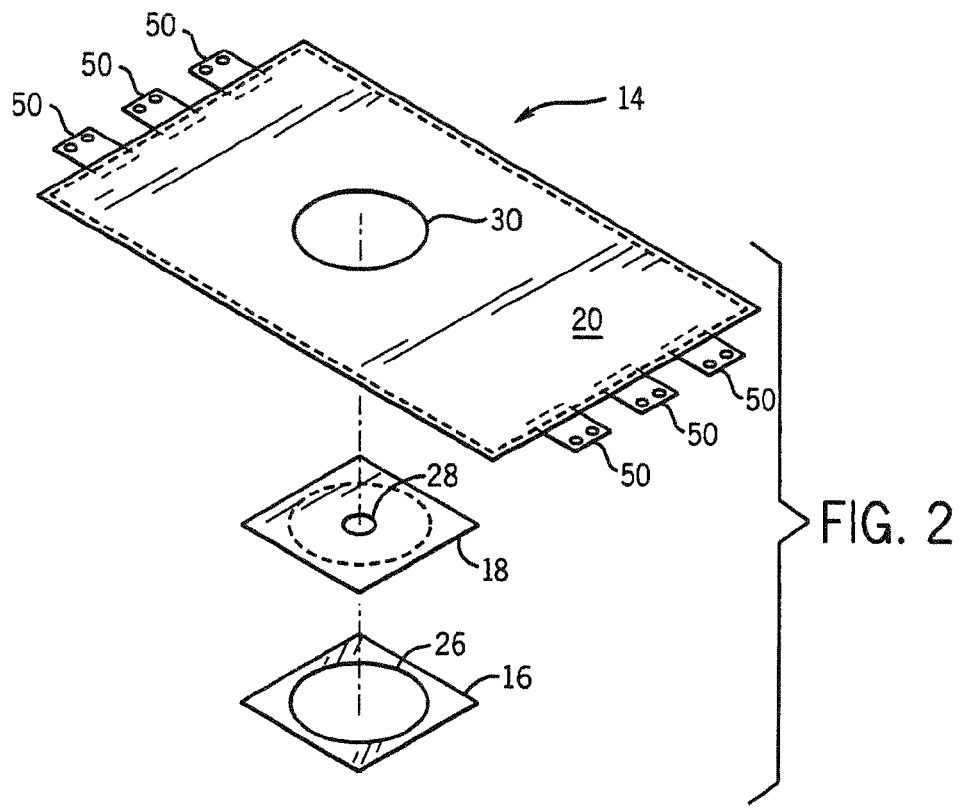
FIG. 2 is an exploded perspective view of a panel assembly of the surgical drape shown in FIG. 1.

The present invention pertains to a fenestrated surgical drape particularly suited for isolating anatomical extremities from other parts of the body during a surgical procedure. The surgical drape has improved liquid and fluid resistance at the seal surrounding the fenestration. In one preferred embodiment of the invention shown and described in detail herein, seal strength and integrity are enhanced by a non-linear seal configuration, multiple narrow, redundant seal regions and the presence of material suitable for heat sealing.

Referring now to FIGS. 1-6 of the drawings, the invention provides a surgical drape 10 including a base drape 12 and a fenestration panel assembly 14, which is made of a sealing panel 16, an apertured panel 18 and a fenestrated panel 20. The base drape 12 is affixed to the panel assembly 14 by an adhesive 22 about the entire periphery of an base drape opening 24. Six cord and tube holding tabs 50 are affixed to either the panel assembly 14 or the base drape 12, for example three at each short end of the fenestrated panel 20, with holes for retaining tubing and/or electrical cords to prevent them from entering the sterile field.

Figure 3:
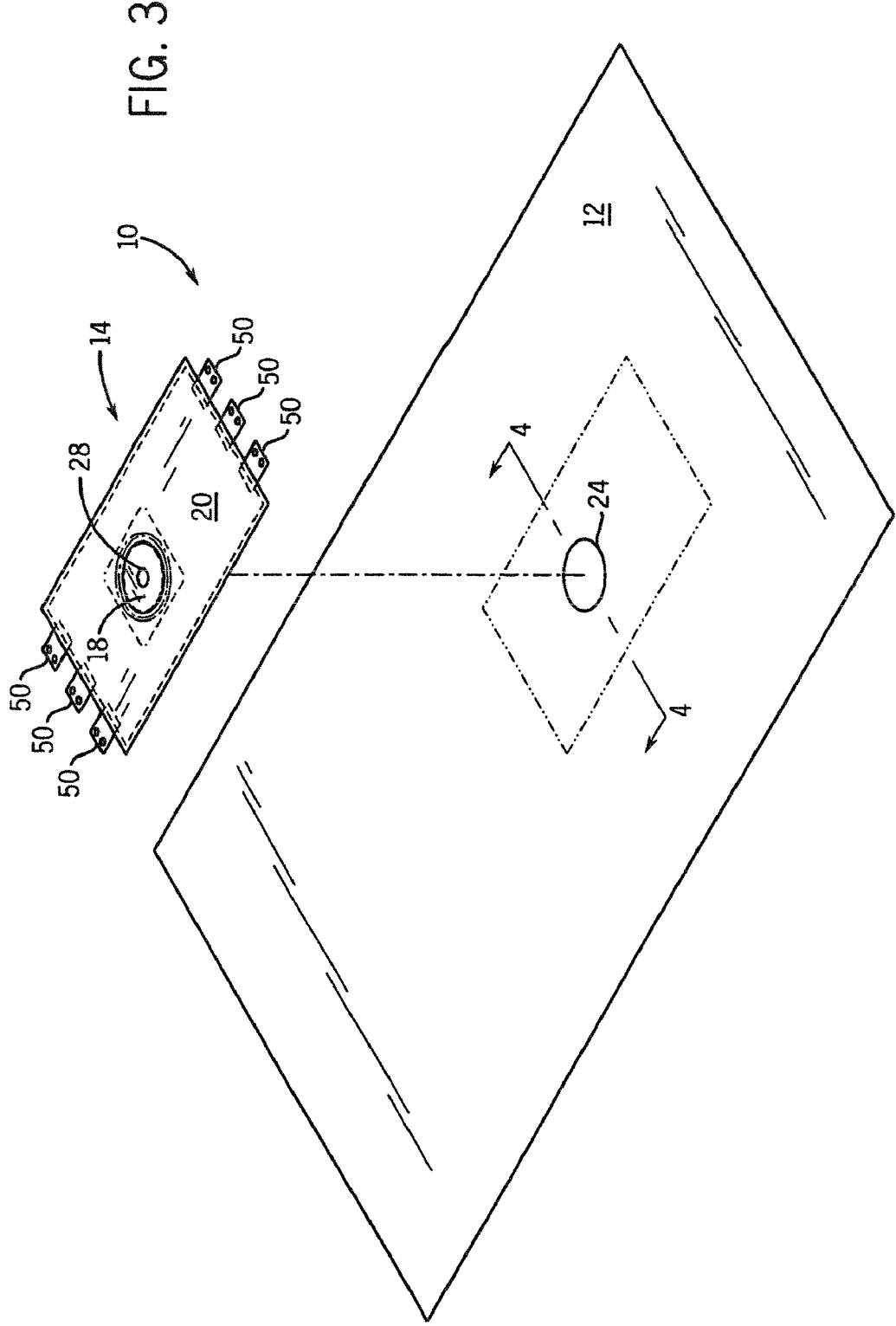
FIG. 3 is an exploded perspective view of the panel assembly of FIG. 2 and a base drape.

As shown in FIGS. 1 and 3, the base drape 12 is a large flexible sheet of material, generally rectangular in the shown embodiment but it can be any suitable shape, provided it is large enough to cover a human body or a sufficient portion of the body adjacent the surgical site to assist in creating a sterile field at the surgical site. The base drape 12 has the opening 24 generally in a central region near the center of the drape, however, it could be located near off center near any peripheral edge of the drape.

Figure 6:
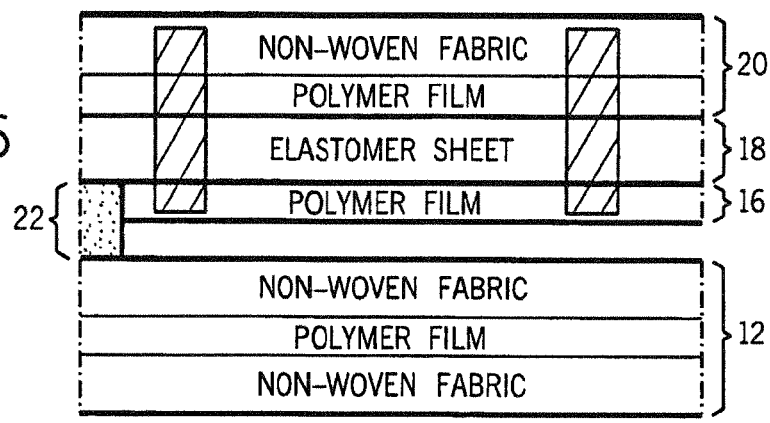
FIG. 6 is an enlarged view showing the layers of material in a preferred embodiment of the surgical drape.

The base drape 12, and the cord tabs 50, can be made of any of a variety of suitable commercially available medical fabric materials. Such medical fabric materials known in the surgical field include without limitation non-woven fabrics. "Nonwoven fabrics" as used herein refers to a single web, or an assembly or laminate of multiple webs, formed of individual randomly laid fibers, for example using a spunlaid, thermobonded, spunbonded, meltblown or bonded carded web process. A laminate of non-woven fabrics is one conventional material in the surgical field that could be used for the base drape 12. A spunbonded/meltblown/spunbonded laminate of polypropylene fibers is one example. Another example of a suitable medical fabric material for the base drape 12 is a combination non-woven fabric and film in which a liquid impervious polymer film is disposed between two non-woven layers. This preferred embodiment is shown in FIG. 6. Such a spunbonded/film/spunbonded laminate material is commercially available as Tiburon.™. from Ahistrom Corporation of Helsinki, Finland.

In any of these composite sheet materials, the individual web layers can be joined together throughout some or all of the surface area and/or along the periphery using any suitable mechanical, thermal, or chemical bonding process, such as point or pattern bonding by the application of heat and/or pressure to the webs. The fibers comprising the various webs can be hydrophilic (liquid absorbing) or hydrophobic (liquid repelling) depending on the material selected. Particularly when a liquid impervious layer is used, such as an inner polymer film, the outer facing layer can be made of hydrophilic fibers, or treated with a surfactant to be absorbent. When a liquid impervious layer is not used in the make up of the base drape 12, the exposed outer layer of the base drape 12 can made of hydrophobic fibers, or treated to be liquid repelling, so that blood or other body fluids present during surgery do not absorb into the base drape 12 and migrate through the material into contact with the patient's body.

The base drape 12 can be constructed of outer webs of different colors or indicia, or a single web with different colors or indicia on each side, to provide visual indication of the difference in material or surface treatments between the sides of the drape. This would help the practitioner identify the proper side to face the patient, for example, if a softer or hydrophobic web was used at the underside of the base drape.

As mentioned, the panel assembly 14 includes three panels. When the panel assembly 14 is attached to the base drape 12, the sealing panel 16 is adjacent the base drape 12 and an opening 26 in the sealing panel 16 is superimposed in registration with the base drape opening 24. The sealing panel opening 26 should be sized slightly larger than the base drape opening 24 so that is circumscribes the base drape opening 24 when assembled.

The sealing panel 16 is preferably a flexible sheet suitable for heat and pressure bonding by heat sealing to at least the other panels of the fenestration assembly 14. A thin polymeric film, such as made of polyethylene, polypropylene, polyester, polyvinylchloride and combinations thereof, can be used as the sealing panel 16 given its ability to bond to other chemically compatible polymeric materials, and particularly non-woven polymer fabrics and elastomers. As mentioned, polymeric films are also preferable because of their liquid impervious property. Any suitable film thickness can be used with a preferred range being 2-5 mils.

The intermediate layer of the panel assembly 14 is the apertured panel 18, which defines an aperture 28. The aperture 28 is superimposed in registration with the sealing panel opening 26 (and opening 30 of the fenestrated panel discussed below) when the panel assembly 14 is assembled. The apertured panel 18 in the preferred embodiment is a stretchable, conformable material suitable to provide a tight seal against the anatomical extremity. Moreover, the aperture itself has a smooth curved inner peripheral edge to avoid gaps between it and the extremity as well as to eliminate areas of increased stress concentrations, as may be present in corners, that can lead to tearing of the aperture edge and disturb the seal with the extremity. The aperture 28 has the least dimension of any of the openings (of whatever type) in the other components of the drape 10, which again is to effect a tight seal with the extremity.

The apertured panel 18 can be made of any suitable sheet having elastomeric properties suitable for surgical applications, including without limitation natural and synthetic rubbers, and being chemically compatible for bonding to the sealing panel 16 and the fenestrated panel 20. A suitable grade of thermoplastic elastomer marketed under the Kraton.®. brand by Kraton Polymers of Houston, Tex. can be used for the apertured panel 18.

The last layer of the panel assembly 14 is the fenestrated panel 20, which defines a fenestration 30 sized larger than the aperture 28 and the base drape opening 24, but slightly smaller than the sealing panel opening 26 such that its inner peripheral edge is slight radially inward thereof. In one preferred form, the fenestrated panel 20 can have a strength component, such as a layer of any suitable natural or synthetic medical fiber material, preferably a non-woven fabric, and more preferably a non-woven fabric as used in the outer layer of the base drape 12 such as a spunbonded web of hydrophilic fibers or fibers having a surface treatment to be absorbent, and can have a sealable component, preferably in the form of a polymer film layer at the underside (facing the fenestration) of the non-woven fabric layer, which is compatible for bonding with the elastomeric aperture panel 18. FIG. 6 illustrates this preferred construction of the fenestrated panel 20.

A suitable bonding agent or technique can be used to affix the panel assembly 14 to the base drape 12. Such a bonding agent can be a double-sided tape or a liquid adhesive, such as a hot melt adhesive, that is chemically compatible with both of the mating materials. In one preferred form, a liquid adhesive is applied in the margin of the perimeter along the film side of the fenestrated panel 20 and along the underside of the apertured panel 18 near its perimeter. At least the adhesive at the perimeter of the fenestrated panel 20 surrounds the entire base drape opening 24 when the panel assembly 14 is adhered to the base drape 12. The adhesive could be replaced by another bonding technique, such as ultrasonic welding.

It should be noted that the openings 24 and 26, the fenestration 30 and the aperture 28 can be of any suitable size and configuration suitable for receiving an anatomical extremity, such as a human arm or leg. The openings 24, 26 and the fenestration 30 are preferably larger than a typical extremity and the aperture 28 is preferably sized smaller than the typical extremity so that it will stretch as it is fit about the extremity and create an air and liquid impervious seal. The openings, fenestration and aperture are depicted as circular, however, they can be any suitable shape, including without limitation oblong, any rectilinear shape or pear/tear-drop shape with asymmetric wider and narrower ends, as may be desired to meet particular dimensions of specific anatomical sites.

An important aspect of the surgical drape 10 of the present invention is the seal arrangement of the layers of the panel assembly 14. Several features of the seal and sealing technique serve to improve the integrity and strength of the seal and thereby improve its effectiveness as a barrier to contaminants. Briefly, these features include the non-linear configuration of the seal, the use of multiple, narrow seal regions circumscribing the aperture and fenestration and the use of a heat sealing technique to join the panels with the application of heat and pressure.

Figure 7:
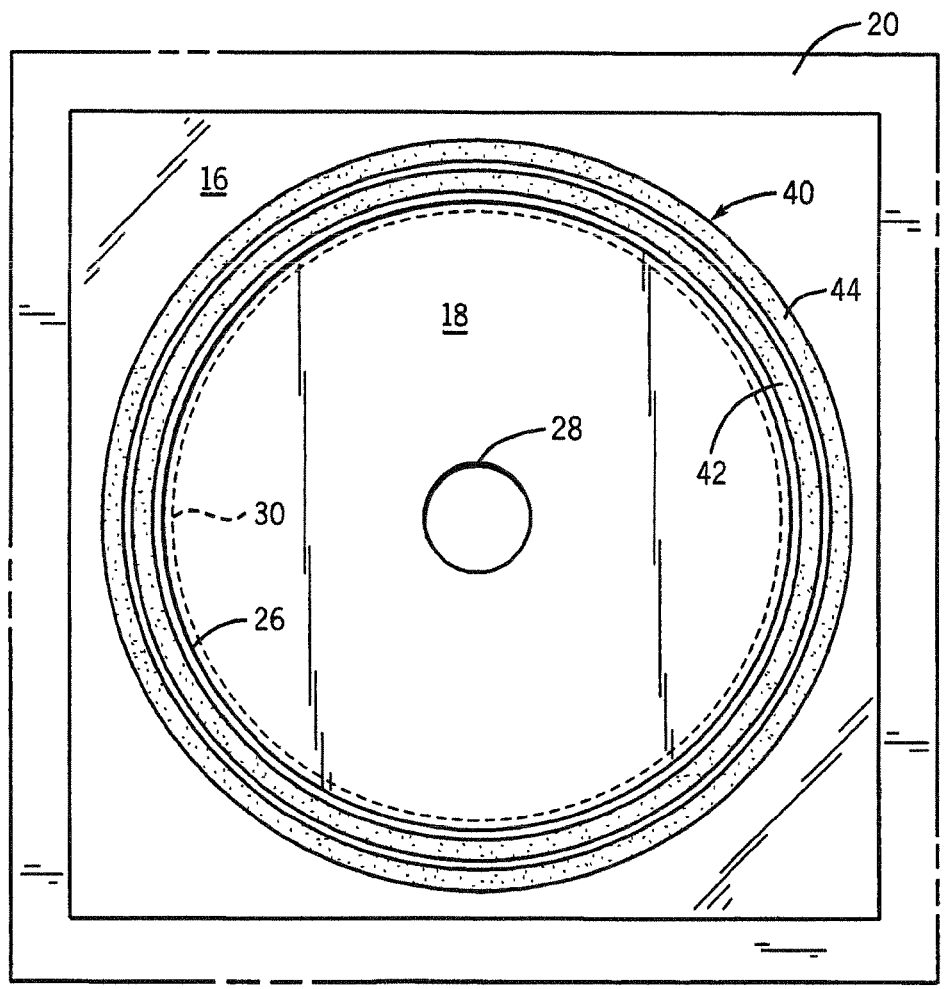
FIG. 7 is a plan view of the panel assembly showing a preferred double-ring seal configuration thereof.

More specifically, one preferred embodiment of the seal 40 is shown in top view in FIG. 7. As can be seen, in this embodiment the seal 40 is formed by two distinct concentric circular regions 42 and 44 circumscribing the fenestration 30, as well as the opening 26 of the sealing panel 16 and the aperture 28. The two seal regions 42 and 44 are spaced apart, with the inner seal region 42 being spaced a radially distance from of the inner peripheral edges of the respective sealing and fenestrated panel openings 26 and 30 and the outer seal region 44 being spaced a radial distance from the inner seal region 42.

The seal 40 thus joins all three panels 16, 18 and 20 of the panel assembly 14 with a liquid impervious thermally and mechanically bonded seal surrounding the opening 26, the aperture 28 and the fenestration 30. The seal provides generally uniform bonding throughout the entire seal regions primarily due to two factors, namely, its non-linear configuration and the use of multiple, narrow seal regions. More specifically, the non-linear configuration eliminates the "hot spots" or areas of increased temperature distribution that often occur at the intersection of linear segments of the seal. Since the seal regions are circular there are no linear segments, and thus no hot spots, resulting in a generally even temperature distribution along the long, here circular, dimension of the seal regions. The use of narrow seal regions reduces or eliminates the temperature variance that can occur in the wall(s) of the sealing element, which can have a lower temperature at the wall center than at the wall peripheral edges, particularly with larger wall thickness dimensions. By using sealing elements with lesser wall thickness dimensions, the entire wall(s) can be heated more uniformly. Since the temperature distribution is more evenly distributed throughout the entire wall thickness, uniform temperature distribution, and thus bonding, can be established along the short (radial) dimension of the seal.

Another feature of the seal 40 that improves its barrier effectiveness is that a redundant seal is established by virtue of having two distinct seal regions 42 and 44. Since each seal region 42 and 44 surrounds the sealing panel opening 26, the aperture 28 and the fenestration 30 entirely, each independently works to provide a barrier. If an unbonded point in the inner seal region 42 were to occur, the outer seal region 44 could provide barrier resistance and vice versa.

Moreover, by using two narrow seal regions, for example two ¼ inch thick seal regions instead of one ½ inch thick seal region, and spacing them apart, the total seal bonding area is increased, by virtue of the larger diameter of the outer seal region 44 caused by spacing the outer seal region radial outward.

To summarize, the seal has more uniform bonding throughout the seal regions in the short radial dimensions. The uniformity of the bonding in the long circular dimensions of the seal regions is improved as well due to the non-linear configuration eliminates hot spots. Further, built-in redundancy of the two seal regions improves the overall integrity of the seal should bonding of one of the regions become compromised. And, the overall bond area is increased. The result is a liquid impervious seal with improved barrier properties to contaminants.

The seal 40 is formed by thermally and mechanically bonding the panels of the panel assembly 14 together with heat and pressure using a heat sealing operation. Prior to the heat sealing operation, the panels 16, 18 and 20 are formed by manual or automated processes, for example, by separately unwinding spools of web material and then forming the openings, fenestration and aperture by independent roll, die or other cutting operations. The fenestrated panel can be cut from a non-woven fiber/film laminate web and the base drape can be cut from a spunbonded/film/spunbonded laminate web. The webs are cut to define individual panels of the desired size and shape. The panels of the panel assembly are bought together in the proper order with the film side of the fenestrated panel facing the apertured panel and the sealing panel being at the other side of the apertured panel. The fenestration and the sealing panel openings are superimposed in registration with the aperture and the panels are joined by forming the aforementioned heat seal about the fenestration. A suitable heat sealing machine, such as that manufactured by Therm-O-Seal, of Mansfield, Tex., can be used. In one preferred process, the seal is formed by applying pressure in the range of about 60-80 psi at 200-350.degree. F. for a cycle time of between about 4-5 seconds.

The cord tabs can then be affixed with adhesive to the film side of the fenestrated panel. And, the panel assembly can then be affixed to the base drape by applying a line of adhesive along the perimeter of the film side of the fenestrated panel as well as to the underside of the apertured panel (in a circular pattern) and then pressing the panel assembly against the base drape with the sealing panel opening, aperture and fenestration superimposed in registration with the base drape opening. The assembled surgical drape is then folded in a suitable configuration, such as a fan and/or roll folds, and suitable indicia (such as unfolding instructions) can be printed or stamped onto the folded drape.

The general procedure for using the surgical drape 10 of the present invention according to one embodiment of the invention is as follows. The patient is laid onto an operating table facing up or in the prone position in preparation for surgery. The drape is unpackaged, unfolded and laid over the patient. The drape is positioned so that the panel assembly 14 is near the extremity of interest. The drape is held on opposite sides of the fenestration and is placed onto the extremity as the extremity is pulled through the base drape opening 24, the sealing panel opening 26, the aperture 28 and the fenestration 30, all of which are in alignment. The drape is positioned up the extremity past the surgical site with the aperture 30 sealing against the extremity near or adjacent the surgical site. The drape is re-oriented as needed to ensure that the rest of the patient's body is covered, or at least a sufficient portion thereof to provide for a sterile field at the surgical site. If necessary, one or more additional drapes, with or without fenestrations and apertures, may be used to cover other non-surgical areas of the patient.

The invention has been described herein with reference to various specific and preferred materials, embodiments and techniques. It should be understood that many modifications and variations to such materials, embodiments and techniques will be apparent to those skilled in the art within the spirit and scope of the invention. Therefore, the invention should not be limited by the above description, and to ascertain the full scope of the invention, the following claims should be referenced.

INDUSTRIAL APPLICABILITY

The invention is useful in fenestrated surgical drapes having an elastomeric apertured panel as part of their construction and designed for use in surgical procedures on limbs and other anatomical extensions.

What is claimed is:

1. A method of making a fenestrated surgical drape, comprising:
   forming a panel assembly including a fenestrated panel defining a fenestration, an apertured panel defining an aperture, and a sealing panel having an opening, wherein the apertured panel is disposed between the sealing panel and the fenestrated panel;
   superimposing the panels such that the sealing panel opening and the fenestration are in registration with the aperture, the aperture having a smaller opening dimension than the sealing panel opening and the fenestration;
   sealing the fenestrated, apertured and sealing panels directly to one another along a non-linear seal path surrounding the fenestration and the aperture; and
   directly affixing the panel assembly to a base drape with the aperture, fenestration and sealing panel opening superimposed in registration with an opening in the base drape.

2. The method of claim 1, wherein the sealing panel is a film, the apertured panel is an elastomeric sheet, and the fenestrated panel is a fiber/film laminate.

3. The method of claim 2, wherein the sealing includes a heat sealing operation.

4. The method of claim 1, wherein the seal path includes at least two spaced apart seal regions.

5. The method of claim 4, wherein the seal path defines two radially spaced concentric circles.

6. A method of making a fenestrated surgical drape, comprising:
   forming a panel assembly including a fenestrated panel defining a fenestration, an apertured panel defining an aperture, and a sealing panel having an opening, wherein the apertured panel is disposed between the sealing panel and the fenestrated panel;
   superimposing the panels such that the sealing panel opening and the fenestration are in registration with the aperture;
   sealing the fenestrated, apertured and sealing panels along a non-linear seal path surrounding the fenestration and the aperture; and
   affixing the panel assembly to a base drape with the aperture, fenestration and sealing panel opening superimposed in registration with an opening in the base drape;
   wherein the sealing panel is a film, the apertured panel is an elastomeric sheet, and the fenestrated panel is a fiber/film laminate.

7. The method of claim 6, wherein the sealing includes a heat sealing operation.

8. A method of making a fenestrated surgical drape, comprising:
- forming a panel assembly including a fenestrated panel defining a fenestration, an apertured panel defining an aperture, and a sealing panel having an opening, wherein the apertured panel is disposed between the sealing panel and the fenestrated panel;
- superimposing the panels such that the sealing panel opening and the fenestration are in registration with the aperture;
- sealing the fenestrated, apertured and sealing panels along a non-linear seal path surrounding the fenestration and the aperture; and
- affixing the panel assembly to a base drape with the aperture, fenestration and sealing panel opening superimposed in registration with an opening in the base drape;
- wherein the seal path includes at least two spaced apart seal regions and defines two radially spaced concentric circles.

* * * * *